(12) United States Patent
Margossian

(10) Patent No.: US 7,699,607 B2
(45) Date of Patent: Apr. 20, 2010

(54) LOCATING AND MEASURING DEVICE OF FACIAL ANATOMICAL PARAMETERS

(76) Inventor: Patrice Margossian, Plaza Talabot, Traverse Max Gaymard / Petro Cocchino BAT.C, Marseilles (FR) 13008

( * ) Notice: Subject to any disclaimer, the term of this patent is extended or adjusted under 35 U.S.C. 154(b) by 253 days.

(21) Appl. No.: 12/024,650

(22) Filed: Feb. 1, 2008

(65) Prior Publication Data

US 2008/0187882 A1 Aug. 7, 2008

(30) Foreign Application Priority Data

Feb. 2, 2007 (FR) .................................. 07 53049

(51) Int. Cl.
*A61C 19/04* (2006.01)
(52) U.S. Cl. .............................. 433/73; 433/68; 433/71; 33/511; 33/513; 33/514
(58) Field of Classification Search ............ 433/54–56, 433/68–69, 72–75, 214, 229; 33/511–514; 600/588–590; 351/200–204, 222, 246
See application file for complete search history.

(56) References Cited

U.S. PATENT DOCUMENTS

| | | | | |
|---|---|---|---|---|
| 1,823,184 A | * | 9/1931 | Beeler | 33/513 |
| 2,048,989 A | * | 7/1936 | Baribeau | 33/513 |
| 2,326,030 A | * | 8/1943 | Hearn | 351/204 |
| 4,547,154 A | | 10/1985 | Puschmann | |
| 4,634,377 A | | 1/1987 | Behrend | |
| 5,059,120 A | * | 10/1991 | Lee | 433/37 |
| 5,724,746 A | * | 3/1998 | Mack | 33/514 |
| 6,109,917 A | | 8/2000 | Lee et al. | |
| 6,386,868 B1 | | 5/2002 | Fujita | |
| 2005/0277086 A1 | | 12/2005 | Arai et al. | |
| 2006/0003285 A1 | | 1/2006 | Kotsuchibashi et al. | |
| 2006/0172254 A1 | | 8/2006 | Shindo et al. | |
| 2007/0157483 A1 | * | 7/2007 | DuMais | 33/512 |

FOREIGN PATENT DOCUMENTS

DE 4025684 A 3/1992
EP 1600117 DA 11/2005

* cited by examiner

*Primary Examiner*—Joe H Cheng
*Assistant Examiner*—Edward Moran
(74) *Attorney, Agent, or Firm*—Lucas & Mercanti, LLP

(57) ABSTRACT

This present invention concerns a locating and measuring device of facial anatomical parameters of a human face. It includes in particular a frame intended to be positioned in front of a face, and a bite yoke mounted on a cross member of the frame, intended to be inserted into the mouth and bitten onto by a patient. In a manner that is characteristic, the invention also includes materialization and positioning for an incisive line, materialization and positioning for a bi-pupillary line, and materialization and positioning for a Camper's plane on at least one profile of the face. The device of the invention finds a particular application in the fields of dental and periodontal reconstruction and repair in accordance with the aesthetic harmony of the face.

15 Claims, 7 Drawing Sheets

LOCATING AND MEASURING DEVICE OF FACIAL ANATOMICAL PARAMETERS

CROSS REFERENCE TO RELATED APPLICATIONS

This application claims the benefit of foreign priority of French Patent Application No. FR 07 53049, filed Feb. 2, 2007, which is hereby incorporated by reference in its entirety.

TECHNICAL FIELD OF THE INVENTION

This present invention concerns a locating and measuring device used for precise measurement of the structural parameters of the face of a subject, so as to assess its aesthetic harmony or, where appropriate, to determine, in a quantifiable manner, the changes necessary to obtain such harmony by surgical and/or prosthetic means.

BACKGROUND OF THE INVENTION

The fields of application of the device of the invention are many, and in particular include odontology, stomatology, orthodontics and plastic and reparative surgery on the human face.

The device of the invention is more particularly designed to facilitate operations for dental and periodontal reconstruction and repair, in accordance with the aesthetic harmony of the face of a subject, as well as operations for aesthetic surgery in the oral field, for re-establishing the aesthetic harmony of the face.

It is considered traditionally, from the medical viewpoint, that a face exhibits a harmonious appearance when a set of criteria, and in particular parallelism, perpendicularity and symmetry are observed.

These criteria particularly concern five individual lines of the face, namely:
- the bi-pupillary line, meaning the line passing through the two pupils of the eyes of the subject,
- the ophriatic line, meaning the line passing through the top edges of the two eyebrows of the subject,
- the bicommissural line, meaning the line passing through the commissures of the lips of the subject,
- the line of the free edges of the teeth of the anterior maxillary or the incisive line, or as known in popular terminology, "the smile line" and
- the line of the anterior maxillary gum contours.

These five lines are completed by the Camper's plane, a plane defined by the two lines joining the sub-nasal points and the porions (or the tragi) on each side, or similarly by the horizontal and the line passing through the sub-nasal point and the porions. The ideal occlusion plane falls in a plane parallel to this Camper's plane.

These five lines must also be perpendicular to the median sagittal plane of the face of the subject, on which ideally the point of the nose, the philtrum and the inter-incisive line all lie.

Although these rules are accepted collectively, the measurements are currently performed in a manner that is approximate and subjective by the practitioners concerned, who base their assessment either on their visual impression or on random measuring methods and freehand, for lack of tools for materialization and objective measurement of the various aesthetic criteria mentioned above.

However the precise location of these aesthetic parameters is essential in order to determine and quantify the asymmetries of the face and/or of the jaw of each patient, to measure these asymmetries, and thus to determine the profiles, dimensioning and orientation of operations for reconstruction to be performed in order to restore the aesthetic harmony of the face of the patient, and in particular the creation of maxillary and/or mandibular dental prostheses, as well as their periodontal integration.

In the area of dental reconstruction, verification and observance of parallelism of the ideal incisive line with the bi-pupillary line and of the perpendicularity of this said ideal incisive line with the median sagittal plane, as well as verification of the symmetry of the dental implantation of the patients in relation to this median sagittal plane, are essential for obtaining aesthetic harmony.

The principal difficulty at present for practitioners in the context of dental and periodontal restoration treatments concerns simultaneous observance of the functional occlusion criteria and the criteria governing the aesthetic harmony of the face.

Observance of these aesthetic criteria cannot however follow directly from observance of the functional occlusion anatomical criteria of the patients treated, since these functional criteria are today mastered and determinable by practitioners by means of tools such as facial arcs and articulators.

Facial arcs are used to record the spatial position of the upper maxillary of the patient in relation to a reference plane known as the Frankfurt plane and then its transfer to the articulators for the creation of complete or partial maxillary prostheses and adjustment of the dental occlusion in harmony with the particular physiology of the patient before implantation in the patients.

These facial arcs, of which documents EP 1 600 117 A, U.S. Pat. No. 6,109,917 and U.S. Pat. No. 7,048,539 B2 give miscellaneous examples, do not allow location of the aesthetic parameters of the face. Neither do they allow diagnosis of dental asymmetries in relation to these aesthetic parameters.

Moreover, since the facial arcs make use of the soft and mobile parts of the face, they do not allow reliable and reproducible recording of the maxillary position. In addition it is very common to observe an asymmetry between firstly the functional reference planes and axes and secondly the bi-pupillary line which is the aesthetic reference, unavoidably falsifying the location of the aesthetic parameters.

We do not know at present of a reliable tool to establish, in a precise and reproducible manner, the location and the measurements of the aesthetic parameters of the face. These measurements are effected in an approximate and subjective manner by the practitioners, who base their assessment either on their visual impression, or on random measuring methods and freehand, for lack of an objective measuring tool.

BRIEF SUMMARY OF THE INVENTION

The aim of the invention is to propose a device that can be used to view and locate on the face of patients the parameters for evaluation of the aesthetic harmony of the face in a simultaneous, reliable and reproducible manner.

The positions of these lines are variable from one individual to another, and the device of the invention is used precisely to locate the lines in relation to each other for each particular individual. These locations are then used for the creation of a prosthesis that is both functional and aesthetic. The aim of the location of at least a part of these lines is therefore to create a prosthetic reconstruction scheme that observes the particular features of the face of the individual while still guaranteeing recognized aesthetic criteria.

Another aim of the invention is therefore to provide a device that allows transfer of the aesthetic parameters located on the face of a patient to the plaster moulds of his own dental arches which, when completed, will be used on the articulators for the manufacture of dental prostheses, thus ensuring the physiological, articular and occlusal functionality of the prostheses and optimal aesthetic harmony for the patient when fitted.

The invention attains its objectives by virtue of a locating and measuring device of facial anatomical parameters of the face of a patient, characterised in that it includes:

a frame intended to be positioned in front of a given face and including at least two uprights, and a bite yoke that includes a securing rod mounted on a cross-member of the said frame, the said yoke being designed to pivot around the said cross-member and around the axis of the securing rod, and being intended to be inserted into the mouth and bitten onto by a patient, and means for materialization and positioning of the incisive line, attached to the frame and designed to slide so as to be aligned with the incisive line of a patient, and means for materialization and positioning of the bi-pupillary line attached to the frame, perpendicular to the vertical uprights, and designed to slide so as to be aligned with the bi-pupillary line of a patient, and means for alignment of the Camper's plane on at least one profile of the said face, attached to the said frame, including at least one rectilinear rod fixed on at least one of the uprights of the said frame and intended to be placed parallel to the Camper's plane of the patient by pivoting of the frame around the cross-member on which the yoke is mounted.

The device of the invention is particularly advantageous to the extent that it can be used to provide the practitioner with a tool for simple and precise evaluation of the aesthetics of the face of a patient, and of any defects, and for measurement of the prosthetic corrections to be made in the context of repair applications or of dental or periodontal reconstruction.

According to the invention, the said means for materialization and positioning of the incisive line, the bi-pupillary line, and the means for alignment of the Camper's plane, are respectively attached to the said frame. In this way, all the aesthetic parameters firstly to be located individually and secondly to be located in relation to the other parameters, are connected to a given fixed support, thus improving the accuracy of the location.

Since the said means for materialization and positioning of the incisive line and of the bi-pupillary line are horizontal, designed to slide perpendicularly on the said frame and preferably mounted on at least one of the uprights of the said frame, it is thus very easy and quick to effect the positioning and the location of these two aesthetic locations on the face of a patient.

By virtue of the invention, the practitioner is able to precisely position, view and then fix, on the frame of the device of the invention, the bi-pupillary line, the incisive line and the orientation of the Camper's plane of a patient. Thus he can then use these locations for making the dental plaster moulds used for creation of prostheses for the patient, so as to ensure observance of the aesthetic parameters of the face after fitting the prostheses.

By virtue of the invention, the practitioner can also perform oral diagnoses by observing any asymmetries or defects of parallelism between certain anatomical elements. For example, the practitioner will be able to locate, with precision, a defect of parallelism of the incisive line with the bi-pupillary line, or indeed a defect of parallelism of the occlusion plane with the Camper's plane. The measurements and observations performed with the device of the invention can therefore then be used to evaluate the needs of the patient and the work to be performed.

According to the invention, the fixing of the bite yoke provides an excellent mobility of the frame in relation to the face of the patient, who bites onto it, and this facilitates the adjustment and the positioning of the device of the invention on the face of the patient.

Advantageously, the means for materialization and positioning of the incisive line, and the means for materialization and positioning of the bi-pupillary line, include means for locking them on the uprights of said frame in a desired location position.

With such a characteristic, one ensures that the positions of the different lines and planes observed on the patient and transferred onto the device of the invention do not move, during the transportation of the device of the invention between the surgery of the dentist and the workshop of the prosthesis maker for example.

According to another advantageous characteristic of the invention, the said bite yoke can, in particular, be fixed onto the lower cross member of the said frame by means of an articulated connecting piece that includes variable locking means that at least allow movement and locking of the said yoke in translation and in rotation on the said cross-member and around the axis of its securing rod.

According to a preferred characteristic, the said bite yoke includes means for recording that are capable of keeping a trace of the position of the dental surfaces of the patient when he bites the yoke.

When the device is used Later to transfer the reconstruction elements onto a plaster model, this characteristic ensures correct positioning of the plaster model mould in relation to the device, this correct position being the one that the patient occupied during the taking of measurements.

According to the invention, the said bite yoke also includes pads for separation of the jaws when the said yoke is bitten by a said patient, so as to provoke in the patient a slight de occlusion that, in contrast to the interior of the mouth, can be used to exactly locate the incisive line at the level of the incisive edge of the upper maxillary. In addition, the open bite also prevents hindering of the practitioner doing the measurements, by the proximity of the lips.

According to another preferred characteristic of the invention, the means for alignment of the Camper's plane form a angle $\alpha$ of between 60° and 80° in relation to at least one of the uprights of the said frame. Such an angle of orientation corresponds advantageously to the extreme average values of orientation of the Camper's plane in relation to a perpendicular plane to the aesthetic plane. This aesthetic plane is located on average 8° above the Frankfurt plane and gives the horizontal plane of the face when the patient looks into the distance. For its part, the Camper's plane (porion/sub-nasal point) is located about 20° below the Frankfurt plane (porion/infra orbital point). By convention, it is also parallel to the occlusion plane of the patient.

In a simple and advantageous manner, the means for alignment of the Camper's plane include at least one rectilinear rod fixed onto at least one of the uprights of the said frame, and lie in a perpendicular plane to the said means for materialization and positioning of the incisive line and of the bi-pupillary line.

This characteristic is advantageous, but the perpendicularity of the rod or rods with the means for materialization and positioning of the incisive line and of the bi-pupillary line is not necessary, since the rod can belong to a plane passing through the upright of the frame and making a non-right angle with the plane of the frame.

It should also be noted that according to a preferred characteristic of the invention, during the use of the device, a rectilinear rod is fixed at identical heights on each of the two uprights. It will be seen that this characteristic allows the easy placement of a transfer tool that will be born by the two rods facing each other on each side of the frame. This then ensures the perpendicularity of the tool with the uprights of the frame.

In a preferred embodiment of the device of the invention, the said means for materialization and positioning of the incisive line and of the bi-pupillary line respectively include a wire mounted so that it slides on the uprights of the frame, and a transparent ruler mounted in at least one slide on at least one of the uprights of the frame.

Means for locking of the said wire and of the said ruler on the uprights of the said frame in a desired location position will be implemented advantageously to lock this wire or this ruler in position.

In one particular embodiment, the device of the invention also includes a means for positioning of the median sagittal axis of the face. The latter is preferably attached to the means for materialization and positioning of the bi-pupillary line, which allows one to simultaneously and precisely locate the bi-pupillary line and median sagittal axis of the face.

In order to further improve this location, the said means for materialization and positioning of the bi-pupillary line also include graduations used to center the said means for positioning of median sagittal axis in relation to the pupils of the said patient.

Finally, in a last alternative embodiment, the device can also include means for materialization and positioning of the incisive line of the lower maxillary in order to allow restoration of the parallelism of the teeth in the lower maxillary with those of the upper maxillary and the bi-pupillary line.

In a preferred manner, these means for positioning of the lower incisive line are identical to those of the incisive line of the upper maxillary, meaning that they include a wire fixed to the uprights of the frame of the device, and graduations for adjusting the position of the said wire.

Another advantageous characteristic of the device of the invention resides in the provision of a transfer tool of the ideal incisive line and of the median sagittal axis onto a plaster moulding of the maxillary arch of the patients teeth, this transfer tool being designed to be placed on the means for alignment of the Camper's plane.

According to an advantageous characteristic of the invention, it can be seen that with the transfer tool positioned on the means for positioning of the Camper's plane, it is such that it also allows the transfer of a line onto the front and the sides of the model, this line belonging to a plane parallel to the Camper's plane, and being parallel to the bi-pupillary line at the front of the model.

This transfer tool can be of a very simple shape. For example, it can be composed of a plate designed to be placed or slid onto the rods for alignment of the Camper's plane, butting up against the uprights of the frame, and including a notch or rear opening used for adjustment of the plate against a plaster moulding of the maxillary placed on the yoke of the device. The plate is also fitted with frontal cut-outs used for positioning the said plate up against the uprights of the frame and, perpendicularly to the uprights of the frame, bearing onto the said means for alignment of the Camper's plane.

The plate will then be positioned around the moulding. By the very constitution of the device of the invention, the plate then defines a plane parallel to the Camper's plane and to the bi-pupillary line. Thus, it is then very easy, using a pencil for example, to use the plate as a guide to establish, on the plaster moulding, a line parallel to the bi pupillary line and also parallel to the Camper's plane. In fact, the line is then parallel to the bi-pupillary line on the front of the plaster moulding and parallel to the Camper's plane on the sides of the plaster moulding.

Advantageously, such a transfer plate can also include a languet or tab, pivoting or fixed, situated in the median vertical plane of the rear notch and therefore virtually in the median sagittal axis when the plate is positioned on the lateral rods of the device, this tab including a groove or a central opening or window used to trace the median sagittal line on plaster maxillary model of a patient, as located previously using the device on the face of the patient.

According to the invention, the transfer plate can also carry a light-emitting device designed to project a line, to trace a median sagittal axis, or a cross, to trace the median sagittal axis at the same time as the parallel to the bi-pupillary line and to the Camper's plane, on the plaster moulding which is then covered with a photosensitive varnish. The change of appearance of the varnish engendered under the effect of the emitted light allows the median sagittal axis to be transferred directly onto the moulding. The light-emitting device is preferably a laser device. The emitting device can possibly be mobile in translation on the plate in order to allow in particular a choice of the size of the traced geometrical figure.

Advantageously, the languet, which is the guidance device, is fitted with through grooves in a T-shape or in a cross-shape used to trace, on to a said plaster maxillary model, a line representing the median sagittal axis of the face of the patient and a line parallel to the bi pupillary line.

BRIEF DESCRIPTION OF THE DRAWINGS

The characteristics of the device of the invention, and the advantages and the particular use of the latter, will emerge more clearly on reading the detailed description that follows, and which is given with reference to the appended figures illustrating the device of the invention in a particular embodiment, and in which.

DETAILED DESCRIPTION OF THE INVENTION

Figure 1:
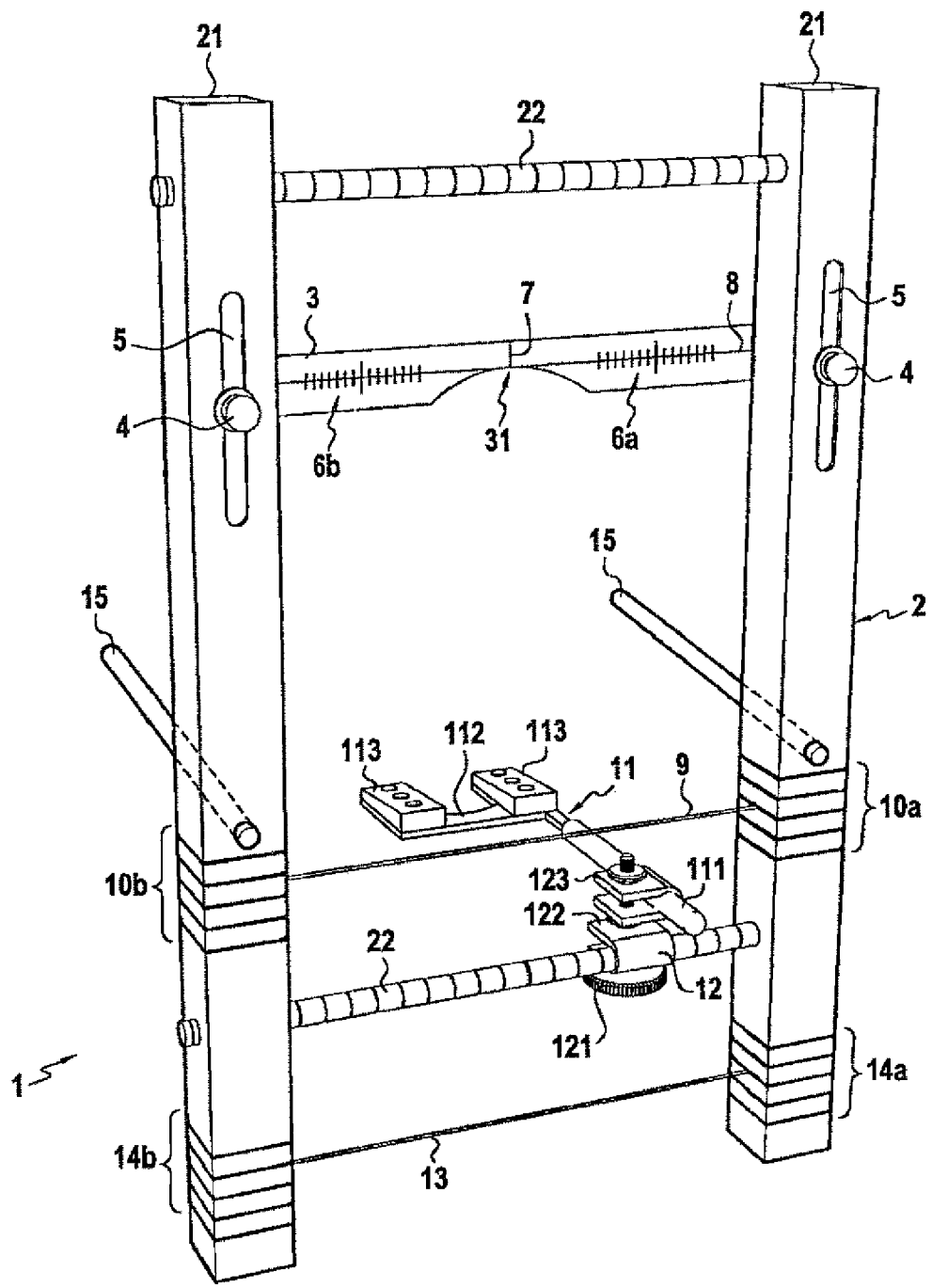
FIG. 1 represents a view in perspective of the locating and measuring device of the invention.
Figure 2A:
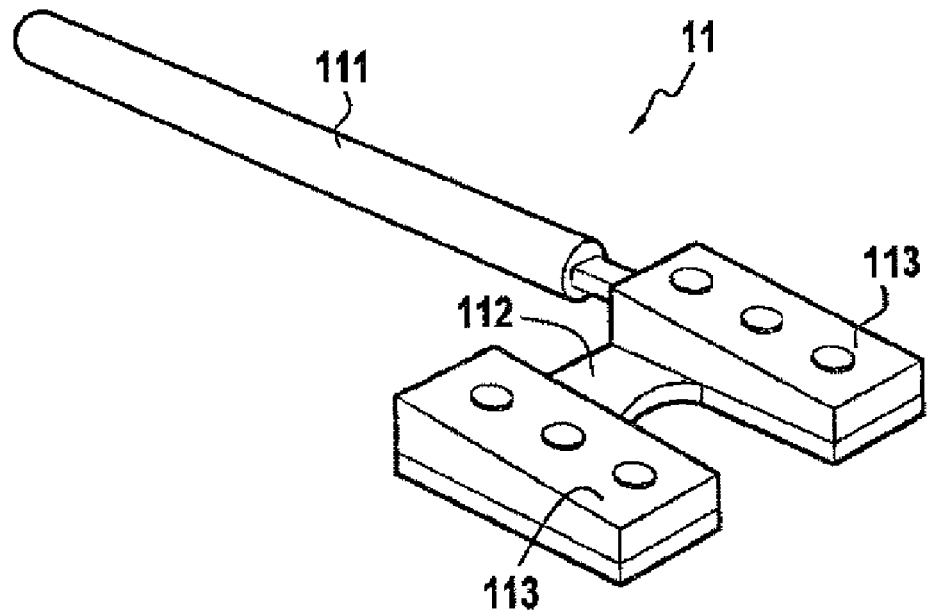
FIGS. 2A and 2B represent, in perspective and in a view from above, a bite yoke designed for the device of the invention.
Figure 2B:
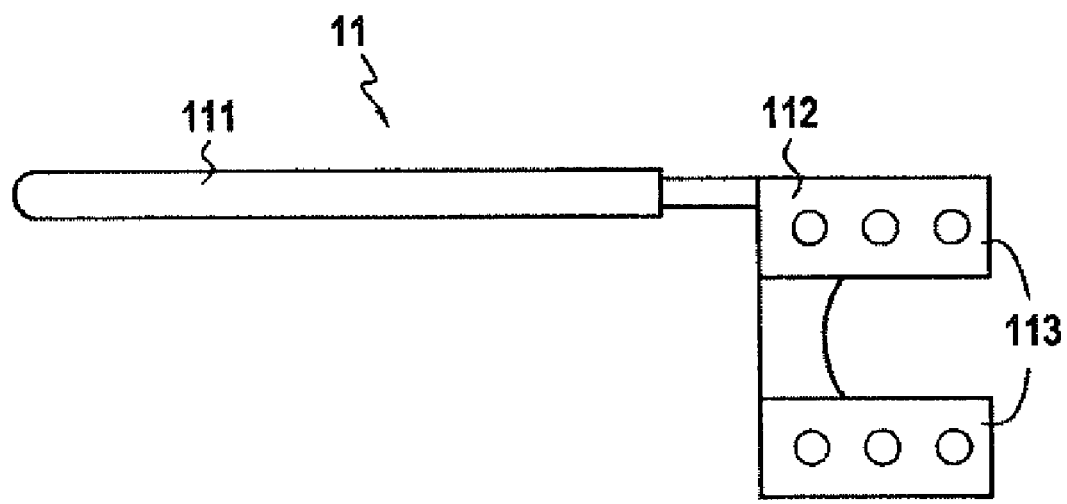

Referring firstly to FIGS. 1, 2A and 2B, the locating and measuring device 1 of this present invention includes a frame 2 composed of two vertical uprights 21 connected together at the level of their upper and lower ends respectively by two cross-members 22. In the embodiment example shown, the uprights 21 are substantially square or rectangular section and the cross members 22 of circular section. However this particular shape of the uprights and cross-members are in no way limiting, and other shapes can be used without interfering with the functions of the device 1.

The dimensions of the frame 2 are chosen so that all types of human face are able to fit within the inside area of the frame, when the device is installed for the establishment of locations or landmarks.

In the top part, the uprights 21 carry a lath 3, also called a ruler, made of Methyl Polymethacrylate (MPMA), better known by its commercial name of Plexiglas®, fixed to the uprights 21 using adjusted and locked means 4. The said means for adjustment 4 include a bolt 41 whose screw is inserted into a through groove 5 formed in the thickness of each of the uprights 21.

At a first end, the screw of the bolts 41 has an operating button. The opposite end of the screw of the bolts 41 is free and passes through an orifice created at the ends of the said MPMA lath 3 so as to support the latter, and to allow its adjustment in height by sliding in the grooves 5 of the uprights. The clamping and locking of the lath 3 is performed by a nut screwed onto the free end of the screw of the bolts 41 and clamping the lath 3 against the rear face of the uprights 22. The lath 3 is such that it can be moved while still remaining perpendicular to the uprights 21. In any way, during the use of the device, it is such that it ensures that the lath 3 is perpendicular to the uprights 21 when this lath 3 is aligned with the bi-pupillary line.

The MPMA lath 3 includes two series of graduations 6a, 6b placed symmetrically in relation to a median vertical line 7 drawn on the lath 3, which itself is equidistant from the uprights 21. A second line 8, perpendicular to the median vertical line 7, is also drawn on the lath 3, preferably centered on the height of the lath 3 and a secant of line 7. The said two series of graduations 6a, 6b are drawn onto this second line 8, which constitutes a means for location and positioning of the bi-pupillary line of a patient. For its part, line 7 forms a means for location and positioning of the median sagittal axis of a patient. The graduations are used to measure the separation of the pupils in relation to the said median sagittal axis and their symmetry in relation to this axis marked by line 7.

In the extension of line 7, the lath 3 includes a nasal notch to allow the frame to be brought as close as possible to the face of the patient during the location and measurement of the particular aesthetic parameters of the said patient, as will be described below.

Above the bottom cross-member 22 of the frame 2, the device 1 also includes means for positioning and materialization of the smile line or incisive line of the upper maxillary. These means consist more particularly of a wire 9, made from synthetic or natural material, fixed to these ends so that they slide on the uprights 21 of the frame 2. In order to facilitate measurement of the vertical position of this incisive line, the said uprights 21 each include graduations 10a, 10b, in which the ends of the wire can be locked after sliding.

In order to achieve a positioning of the frame 2 that is totally fixed during the taking of measurements, the device of the invention includes an original means for positioning of the frame 2 relative to the face of the patients, which consists of a bite yoke 11 attached to the bottom cross-member 22 of the frame 2 and mobile on and around the latter by means of an articulated link 12 designed to slide and pivot on the said cross-member 22.

As shown in FIGS. 2A and 2B, the bite yoke 11 includes a rectilinear rod 111 used for fixing the yoke 11 onto the lower cross-member 22 of the frame 2 by an articulation 12, and a bite plate 112 at one end of the said rod.

The rod 111 is preferably fixed outside the extension of one edge of the plate 112. This provides a better view of the incisor teeth of the patients during measurements taken using the device of the invention, by lateral separation of the articulation 12 in relation to the incisor teeth of the patient, the lower edge of which must be viewed and read in order to materialize the incisive line and its position, as will be described below in FIG. 3.

The bite plate 112 is preferably of relatively small length compared to those of the yokes usually employed in the dental field. Tt has substantially a U shaped whose two branches, according to a specific characteristic of the invention, also carry two de-occlusion pads 113, placed on the upper face of the said branches. These pads 113 have substantially a triangular rectangle shape, of smaller thickness at the end of the branches of the plate. The maximum thickness of the said pads 113 is preferably of the order of 5 mm. These pads advantageously have locating and/or recording means of the exact position at which the patient bites. These means, which can be created using elements for moulding of the back teeth at the level of the pads, or again with recording means, are then used to position the plaster moulding on the frame of the device of the invention in an exact manner.

The articulated link 12 includes a clamping screw 121, on the rod of which are screwed two U shaped brackets 122, 123, the bracket 122 being clamped onto the cross member 22 and bracket 123 being clamped onto the rod 111 of the bite yoke 11. The screw 121 includes, at one end, a clamping wheel by means of which it is possible to simultaneously increase or decrease the clamping of the brackets 122, 123 on the cross-member 22 and on the yoke 11 respectively, and to lock their position.

In addition to the wire 9 and the graduations 10a, 10b for positioning and materialization of the upper incisive line, the device 1 of the invention includes a second wire 13, also fixed onto the uprights 21 of the frame 2 and located under the lower cross-member 22 carrying the yoke 11. This second wire 13 is used, in certain clinical cases that so require, to locate the incisive line of the lower maxillary. Graduations 14a and 14b, identical to graduations 10a and 10b, are also formed on the uprights, and allow the adjustment and measurement of the level of this lower incisive line.

Finally, the device of the invention also includes lateral rods or arms 15 inserted at one of their ends into the uprights 21 of the frame 2 and which, in FIG. 1, lie in a plane perpendicular to the plane of the frame 2. It can be seen that the extension of this rod 15, perpendicular to the plane of the frame, is not obligatory. In particular, in order to be able to adapt the frame regardless of the size of the head of the patient and keeping to a minimum size of the frame, it will be judicious to locate these rods 15 so that the planes that contain them make an angle other than 90° with the plane of the frame on each side of the frame and toward the outside of the latter. With these diverging rods, the placement of the face of the patient between them is facilitated.

The function of the rods 15 is to locate, on the profiles of the patients' faces, a plane that is parallel to the anatomical Camper' plane CP, which passes through the porion and the sub-nasal point. This is why the said rods form an angle $\alpha$ of between 60° and 80° with the uprights 21, an angle which corresponds to the mean anatomical inclination variations of the Camper's plane CP.

In an advantageous embodiment of the invention, a set of several holes are provided on each of the two uprights 21 of the frame in order to be able to receive each of the rods 15. These holes are advantageously materialized by a multiplicity of orifices created in each of the uprights 21, these orifices being such that the rod, placed in one of these orifices, makes an angle α of between 60° and 80° with the upright 21 on which it is placed. The option to change the height of the rods 15 allows easier location of the Camper's plane based on the principle that the closer the rod is in height to the Camper's plane (sub-nasal/porion line) observed on the patient, the easier will be the alignment of the rod with this imaginary line.

The full method of use of the device of the invention 1 will now be described with reference to FIGS. 3 to 6B, in the context of a repair or reconstruction operation of the upper maxillary. One of the major difficulties of these operations is in the preparation of dental prostheses that are made up to observe the parallelism of the ideal incisive line and of the gums with the bi-pupillary line, and the parallelism of the inter-incisive lines with the median sagittal axis of the face. The device 1 of the invention is used to evaluate the exact positioning of the bi-pupillary line, the median sagittal axis and the incisive line on the face of a patient.

Figure 3:
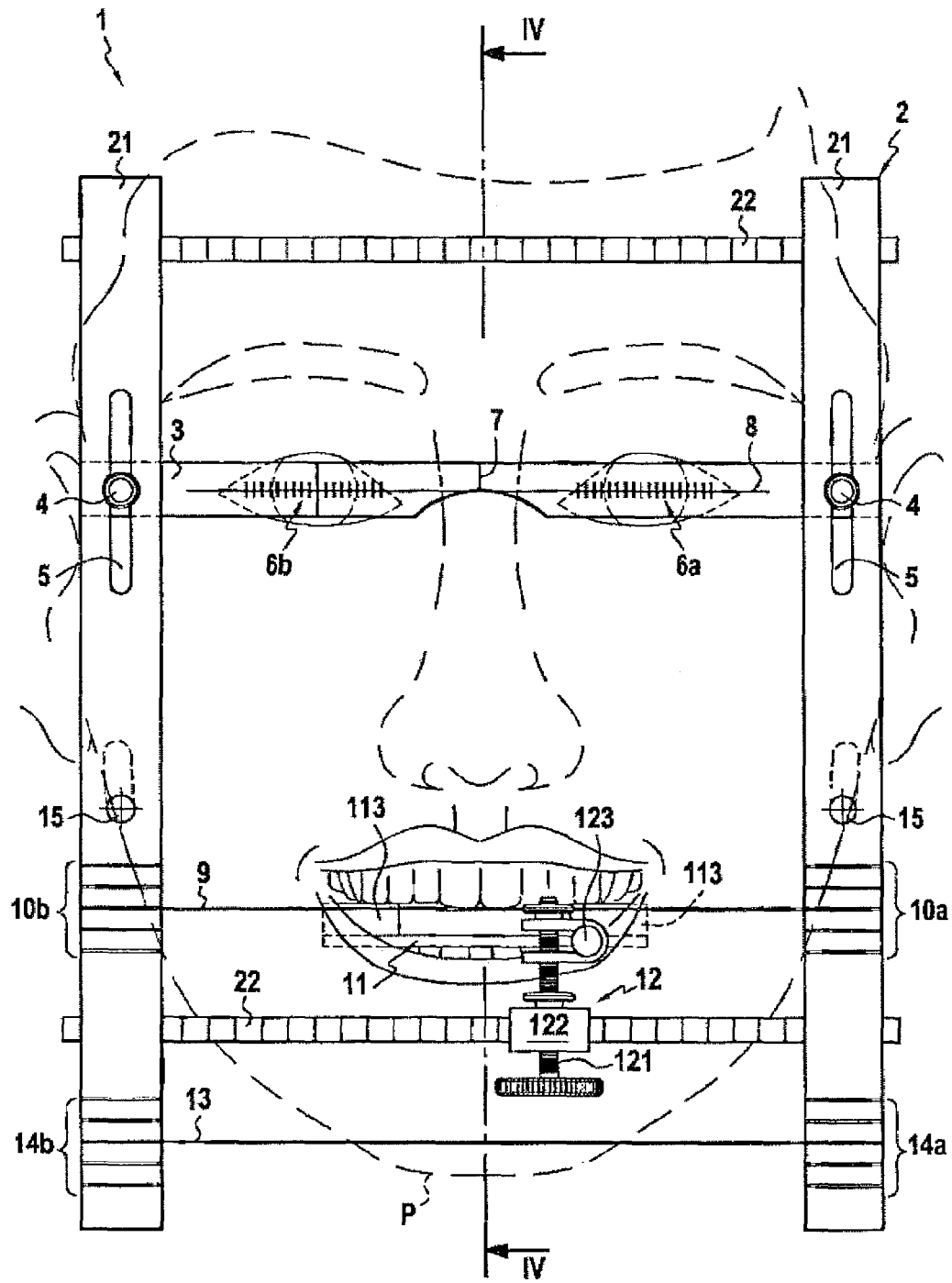
FIG. 3 represents, in a front view, the method of use and location of the aesthetic parameters on the face of a patient using the device of the invention.
Figure 4:
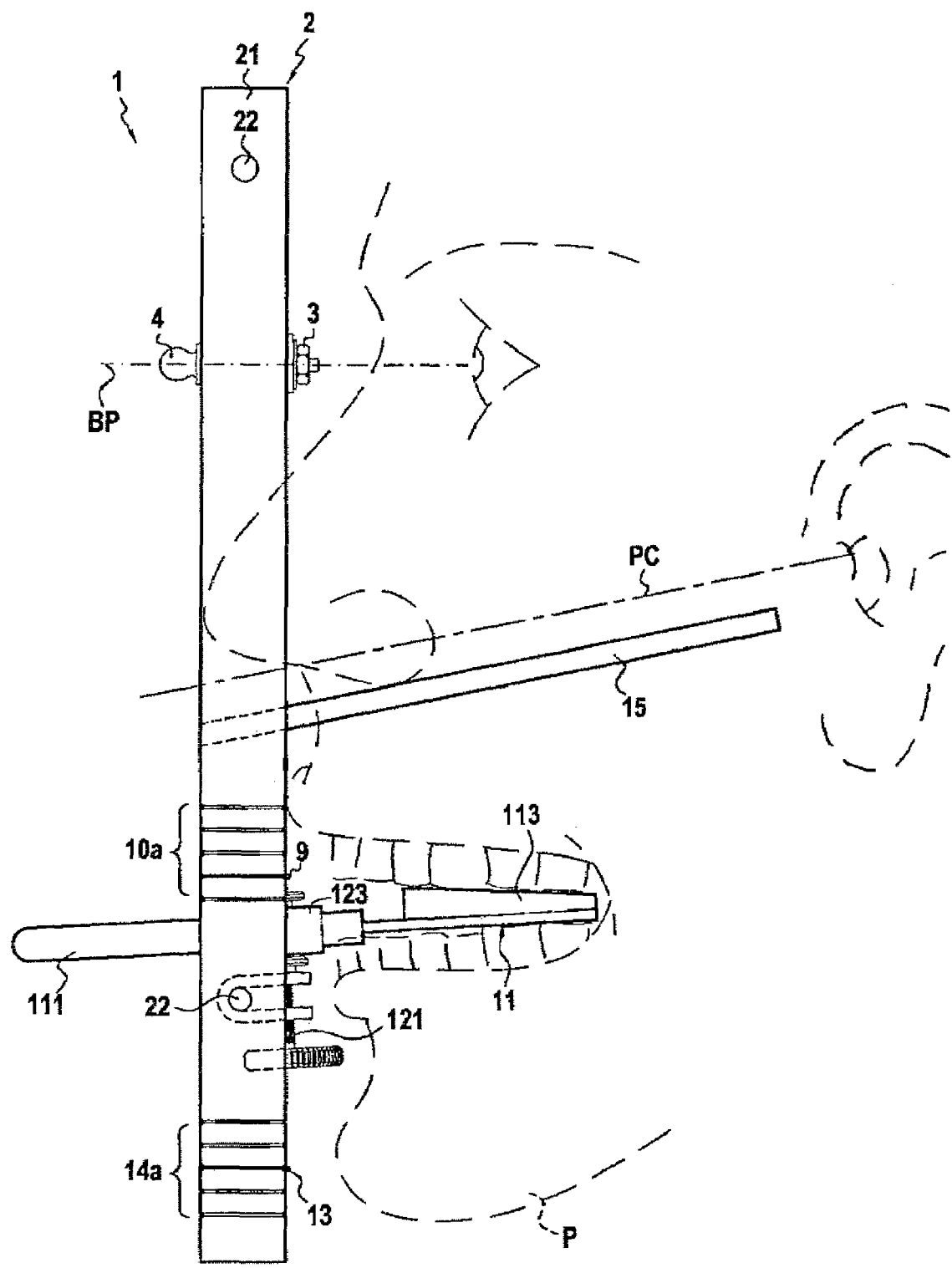
FIG. 4 represents, in a view in profile, the method of use and location of aesthetic parameters on the face of a patient using the device of the invention.

Referring first to FIGS. 3 and 4, the device 1 is positioned in front of the face of a patient P with insertion of the bite yoke into the mouth of the patient. The articulation 12 of the yoke 11 on the lower cross-member 22 of the frame is then loosened so as to allow sufficient mobility of the frame 2 and of the yoke 11 for correct adjustment of the yoke in the mouth. The patient must bite on the yoke 11 between the upper and lower molars.

The presence of the pads 113 on the plate 112 of the yoke then gives rise to a de-occlusion of the upper and lower maxillary. Preferably, before inserting the yoke 11 into the mouth, a fine coat of wax or other moulding material is deposited onto the pads 113, and used to personalize the bite planes to the dental arches of the patient P and also to locate the exact position of the bite during the later positioning of the plaster moulded model. At the same time the yoke is held firmly in position in the mouth of the patient P. It will be observed that the yoke must be bitten on at the level of the back teeth, in order to ensure the stability of the device and the reliability of the position measurements in relation to the face of the patient. The position of the frame 2 is then adjusted in relation to the face of the patient by pivoting and sliding the frame on the lower cross-member 22 at the level of the articulation 12, and sliding of the said articulation on the rod 111 of the yoke 11 so as to place the frame 2 as close as possible to the face of the patient P, and so that firstly the vertical line 7 drawn on the lath 3, also called the ruler, is aligned with the median sagittal axis S of the face of the patient P and secondly that the lateral rods 15 are parallel to the Camper's plane CP, as shown in FIG. 4.

In the specific example of FIG. 4, the observed patient does not satisfy the recognized aesthetic criteria concerning the parallelism between the Camper's plane and the occlusion plane. These are current situations, but which can be resolved precisely during the dental reconstitutions by prosthetic techniques, by virtue of the device of the invention.

Once this position has been found, the wheel of the rod 121 of the articulation 12 is tightened up in order to lock the position of the frame 2, which then remains in equilibrium by virtue of the force applied by the jaw of the patient P on the yoke 11.

The position in height of the lath 3 is then adjusted in relation to the face using the bolts 4 in the grooves 5 to position and materialize the bi-pupillary line. This is achieved by using the line 8 drawn on the lath 3 and by aligning this line with the pupils of the eyes of the patient P. By construction, the lath 3 moves in a direction parallel to the uprights of the frame, remaining perpendicular to the latter. With this alignment completed, the bolts 4 are tightened up, and it is then possible to determine, by virtue of the graduations 6a and 6b, the exact separation of the pupils in relation to the median sagittal axis S materialized by line 7 on the lath 3 and, where appropriate, to measure the asymmetries between the two eyes of the patient, or more simply to recenter the frame correctly.

With the bi-pupillary line fixed by line 8, the smile line or incisive line of the upper maxillary is then located by means of wire 9. For this location, the de occlusion generated by the pads 113 of the yoke 11 play an important role in that they allow an examination of the lower edge of the incisor teeth that is not interfered with by the articulation 12 for fixing of the frame 2 and the yoke 11. It is thus possible to exactly align wire 9 and the incisive line of the patient, and to read off the exact position of this line by means of the graduations 10a, 10b on the uprights 21 of the frame.

With the bi-pupillary line and the incisive line located on the face of the patient, the practitioner can then diagnose any asymmetries, which he will be able to correct progressively.

Figure 5A:
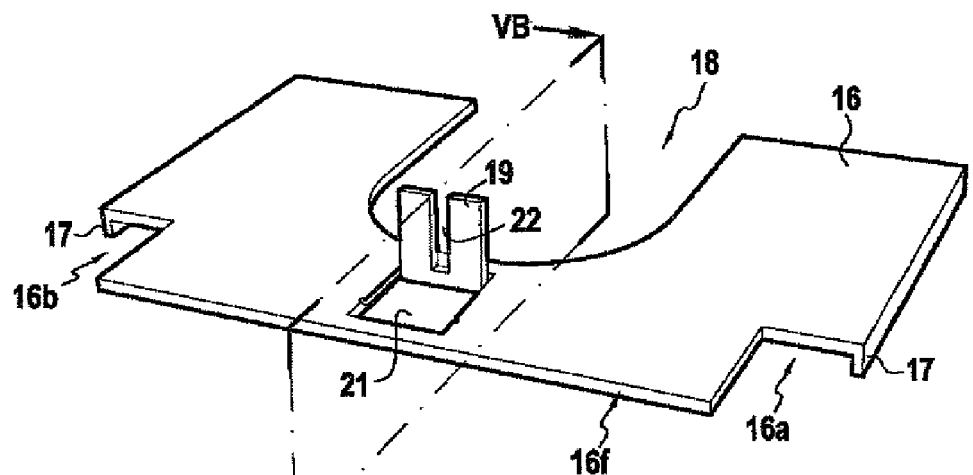
FIGS. 5A to 5C respectively represent, in perspective and in a view from the left, a first embodiment of a locations or landmarks transfer plate of the device of the invention, and a second embodiment of a locations transfer plate of the device of the invention.
Figure 5B:
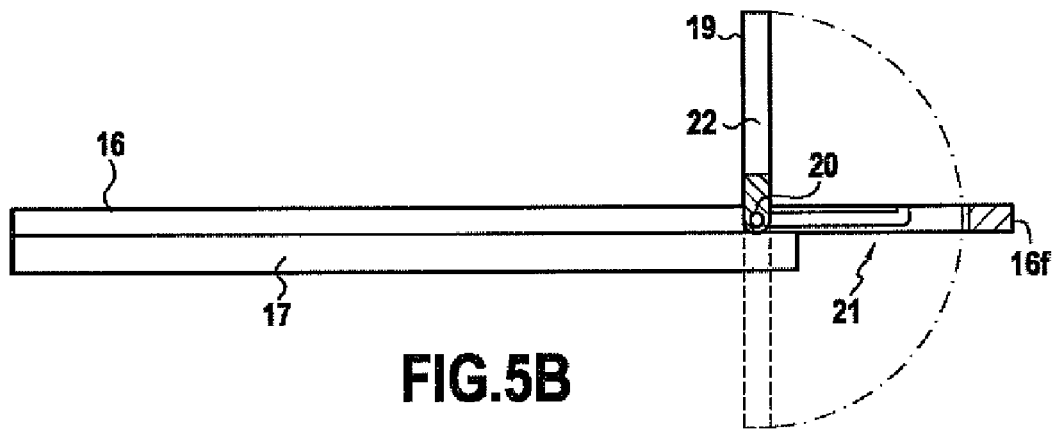
Figure 5C:
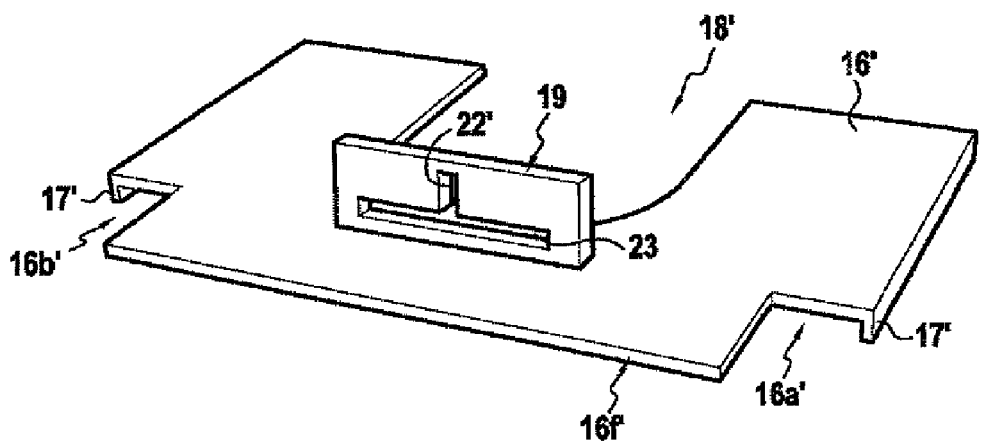

The device of the invention also includes a transfer tool of aesthetic locations or landmarks onto a plaster maxillary moulding used for the creation of dental prostheses, in order that the latter may create a pleasing aesthetic impression of the observed face after they are put in place. Two embodiments of this transfer tool are represented in FIGS. 5A to 5C, and their use is described in FIGS. 6A and 6B.

In the two embodiments presented in FIG. 5, the transfer tool consists of a plate 16 or 16' respectively, of generally rectangular shape and whose length is appreciably equal to the maximum separation between the lateral rods 15 of the frame and of any width, including two frontal rectangular cut-outs 16a, 16b (or 16a', 16b') at the corners of the plate 16 or 16'. Moreover, the plate also includes, on its two lateral edges 16c, 16d (or 16c', 16d'), languets 17 or 17'.

These cut-outs 16a, 16b (or 16a', 16b') and these languets 17 or 17' are designed to allow sliding and stabilisation of the plate 16 or 16' on the rods 15 of the frame 2 of the device and insertion of the frontal edge 16f or 16f' between the uprights 21 until they butt up against the said uprights 21. The length of the cut-outs 16a, 16b (or 16a', 16b') is preferably chosen so that the frontal edge 16f or 16f' of the plate passes beyond the uprights 21 when the plate is butting up against the uprights, by 2 to 3 cm.

Figure 6A:
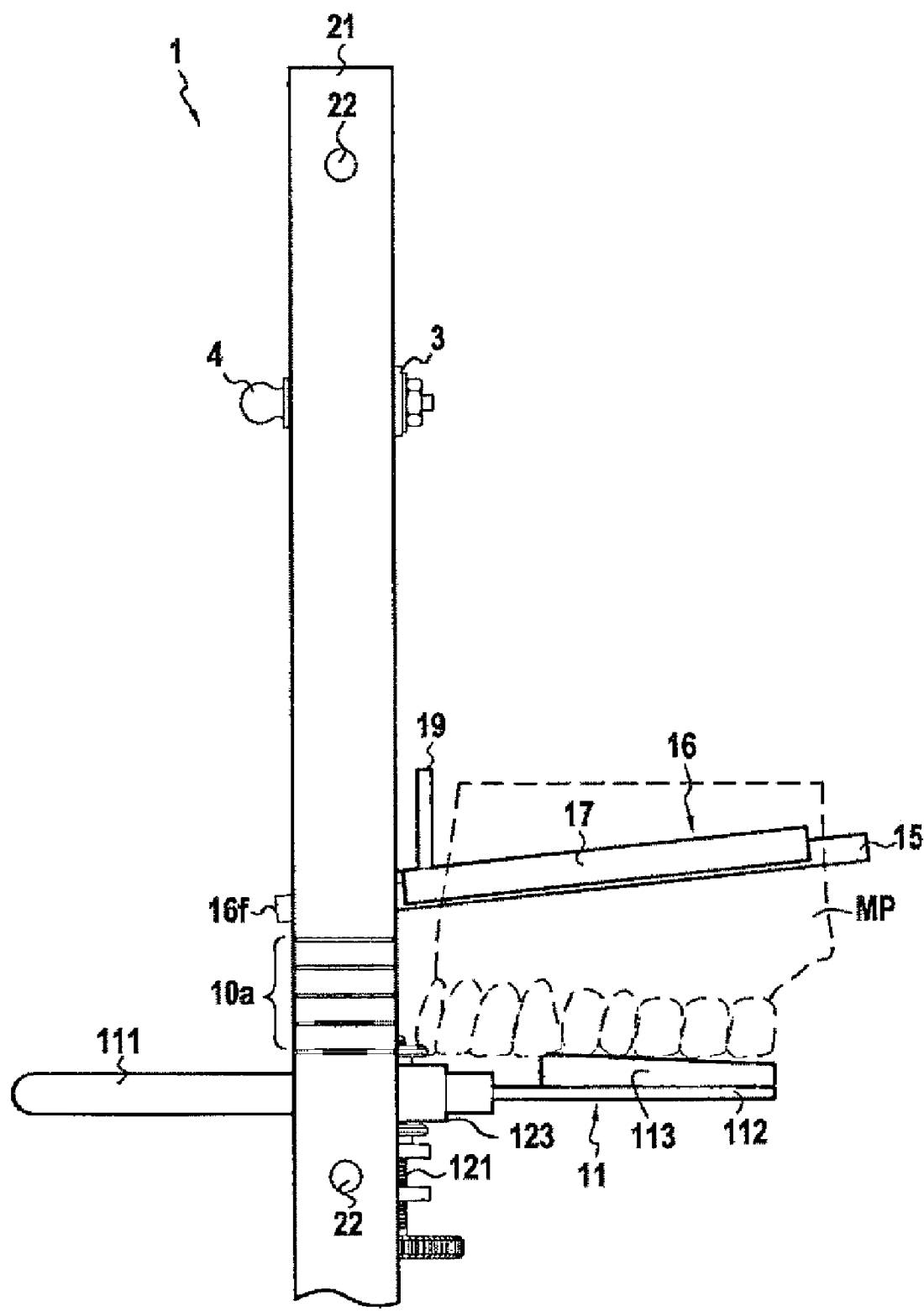
FIGS. 6A and 6B represent, in a view in profile and in a front view, the method of transfer of aesthetic reconstruction lines onto a plaster maxillary model using the device of the invention and from the aesthetic data read from a patient.
Figure 6B:
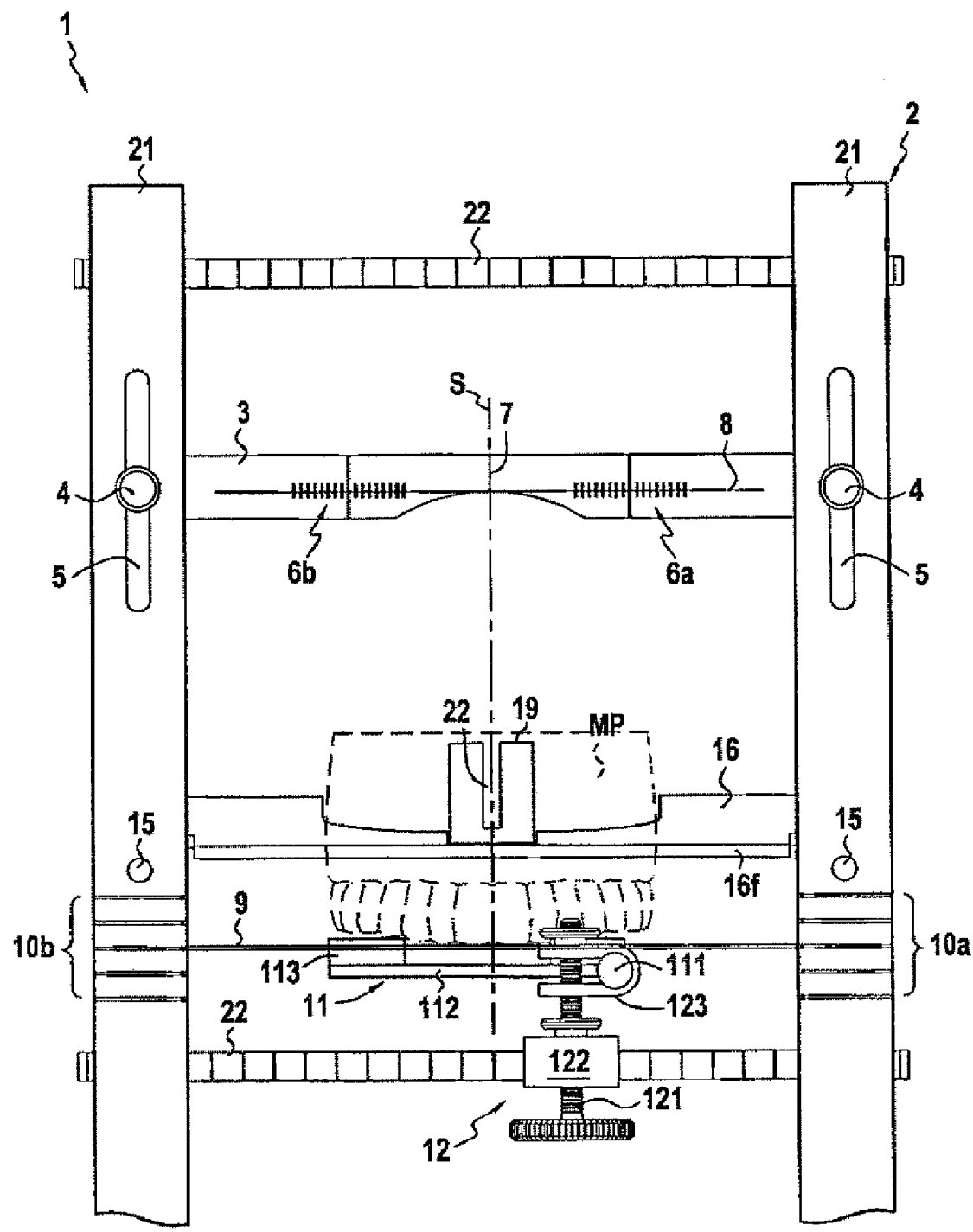

The plate 16 or 16' also includes a rear opening 18 or 18' of a shape that is designed to allow the positioning in this opening 18 or 18' of a plaster maxillary model as represented in FIGS. 6A and 6B. This opening 18 or 18' is centred in the length of the plate 16 or 16' and its front edge, appreciably circular in the figures, is appreciably located in the plane of the rear face of the uprights 21 of the frame 2 of the device, when the plate 16 or 16' is butting up against the uprights 21.

In FIGS. 5A and 5B, the plate 16 includes pivoting languet or tab 19 located between the opening 18 and the frontal edge of plate 16f. This languet 19 is mounted to pivot and slide around two lugs 20 placed in a groove or opening created in the edges of a rectangular cut-out 21 formed in the plate (16), and includes a central groove or opening 22 located in the median transverse plane VB of the plate, this plane VB also being median to opening 18.

When perpendicular to plate 16, the languet 19 is used to transfer, onto plaster maxillary models, a line representing the median sagittal axis S represented by line 7 on the lath 3 of the device. Once the languet is again parallel to the plate 16, the plate 16 itself can be used to transfer a line parallel to the bi-pupillary line BP, materialized on the device 1 of the invention by line 8 on the transparent lath 3 and, ideally, wire 9.

In order to perform this transfer, one proceeds as shown in FIGS. 6A and 6B and as explained below.

In FIG. 5C, the plate 16' includes a fixed tab 19' located between the opening 18' and the frontal edge of the plate 16f'. This tab 19' is mounted in a fixed manner, for example, using two screws through the plate 16'. It includes two through grooves or openings 22' and 23 in the central region of the tab 19' located in the median transverse plane VB of the plate, this plane VB also being median to opening 18'.

Here, the tab 19' is used on its own to transfer, to the plaster maxillary models, a line representing the median sagittal axis S represented by line 7 on the lath 3 of the device, as well as a line parallel to the bi-pupillary line BP, materialized on the device 1 of the invention by line 8 on the transparent lath 3 and wire 9. The plate is used to transfer a line parallel to the Camper's plane onto the sides of the model.

An explanation follows on the manner of transferring locations or landmarks taken on the patient to a moulded plaster model using the plate of FIGS. 5A and 5B. Plate 16 is placed on the rods 15 of the frame 2 and is locked to butt up against the uprights 21 of the frame 2 at the level of the angled cut-outs 16a, 16b. Then a plaster maxillary model MP is placed on the pads 113 of the yoke 11 of the device 1 by virtue of the indenting of the posterior sectors on the registration wax that covers the pads 113 of the said yoke, on which no change has been made to the adjustments after taking the locations on the face of the patient. Thus the model MP is located exactly in a position identical to that of the upper maxillary of the patient during the taking of locations (FIGS. 3 and 4). The model MP is then located in the opening 18 of the plate 16 resting on the lateral rods 15 of the device.

Then, using a pencil, a horizontal line is transferred onto the model MP, by making the pencil slide along the plane of the plate 16, and then, after lifting the languet 19, a vertical line is transferred by guiding the pencil in the groove or opening or central window 22 of the pivoting languet 19. By pivoting the said languet 19 downwards, it is then possible to extend the vertical line below the plate 16. These two lines then allow the prosthesis maker to have an exact location for the parallel to the bi-pupillary line, the Camper's plane, and the median sagittal axis of the patient on the plaster model MP.

Once these horizontal and vertical lines have been traced by the practitioner on the plaster maxillary model MP, the latter then has an orthogonal location whose horizontal axis is parallel to the bi-pupillary line, and whose vertical axis is perpendicular to the latter, which allows one to create a prosthesis dental that will result in a perfectly aesthetic result when fitted, allowing the patient to retrieve an aesthetically normal smile.

In addition, the plate 16 being placed on the rods parallels to the Camper's plane, this provides an opportunity to trace onto the sides of the plaster model a line that is also parallel to the Camper's plane, as represented in FIG. 6A. In an ideal aesthetic case, this line, parallel to the Camper's plane, according to ideal morphological criteria, is parallel to the ideal occlusion line. This is then used for reconstruction when needed. On FIG. 6A, the shown jaw does not need teeth reconstruction but it can be noted that the occlusion plane is not parallel to the Camper plane. The corresponding patient does not present the ideal morphological parameters.

The invention claimed is:

1. A locating and measuring device of the anatomical facial parameters of a human face, characterized in that it includes:
   a frame capable of being positioned in front of a patient's face and including at least two uprights, and
   a bite yoke that includes a securing rod mounted on a lower cross-member of said frame, said yoke being designed to pivot around said cross-member and around the axis of the securing rod and capable of being inserted into the mouth and bitten onto by the patient, and
   means for materialization and positioning of an incisive line, being attached to the frame and designed to slide so as to be aligned with the incisive line of the patient, and
   means for materialization and positioning of a bi-pupillary line attached to the frame, perpendicular to the vertical uprights, and designed to slide so as to be aligned with the bi-pupillary line of the patient, and
   means for alignment of a Camper's plane on at least one profile of said face, attached to said frame, and including at least one rectilinear rod fixed onto at least one of the uprights of said frame and capable of being placed parallel to the Camper's plane of the patient by pivoting of the frame around the cross-member on which the yoke is mounted.

2. A device according to claim 1, characterized in that the means for materialization and positioning of the incisive line, and the means for materialization and positioning of the bi-pupillary line include locking means on the uprights of said frame in a desire position.

3. A locating and measuring device according to claim 1, characterized in that said bite yoke is fixed onto the lower cross-member of said frame by means of an articulated connecting piece that includes variable clamping means that at least allow movement and locking of said yoke in translation and in rotation on said cross-member and around the axis of its securing rod.

4. A locating and measuring device according to claim 1, characterized in that said bite yoke includes recording means that are capable of keeping a trace of the position of the dental surfaces of the patient when he bites onto the yoke.

5. A locating and measuring device according to claim 1, characterized in that said bite yoke includes pads for de-occlusion of the jaws when said yoke is bitten onto by a said patient.

6. A locating and measuring device according to claim 1, characterized in that said means for alignment of the Camper's plane form an angle of between 60° and 80° in relation to at least one of the uprights of said frame.

7. A locating and measuring device according to claim 1, characterized in that said means for materialization and positioning of the incisive line and of the bi-pupillary line respectively include a wire mounted so that it slides on the uprights of the frame, and a transparent ruler mounted in at least one slide on at least one of the uprights of the frame.

8. A locating and measuring device according to claim 1, characterized in that it also includes a positioning means of the median sagittal axis of the face.

9. A locating and measuring device according to claim 8, characterized in that said position means of the median sagittal axis of the face is attached to said means for materialization and positioning of the bi-pupillary line.

10. A locating and measuring device according to claim 8, characterized in that said means for materialization and positioning of the bi-pupillary line include graduations used to center said positioning means of the median sagittal axis in relation to the pupils of said patient.

11. A device according to claim 1, characterized in that the device includes a transfer tool for a line parallel to the bi-pupillary line, which is parallel to the ideal incisive line, onto a plaster maxillary model of the patient's teeth said transfer tool being designed to be positioned on the positioning means of the Camper's plane.

12. A device according to claim 11, characterized in that, the transfer tool being positioned on the positioning means of the Camper's plane, such that it also allows the transfer of a line onto the front and sides of the model, the line belonging to a plane parallel to the Camper's plane and being parallel to the bi-pupillary line at the front of the model.

13. A locating and measuring device according to claim 11, characterized in that said transfer tool includes a plate fitted with a rear opening used for adjustment of the plate around said plaster maxillary model placed on the yoke of the device, as well as frontal cut-outs used for placement of said plate up against the uprights of the frame and, perpendicularly to the uprights of the frame, bearing onto said means for alignment of the Camper's plane.

14. A locating and measuring device according to claim 13, characterized in that said plate includes a pivoting or fixed languet or tab equipped with at least one central groove or opening used to trace, onto a said plaster maxillary model, a line representing the median sagittal axis of the face of the patient.

15. A locating and measuring device according to claim 14, characterized in that the languet or tab is fitted with grooves in a T-shape used to trace onto said plaster maxillary model a line representing the median sagittal axis of the face of the patient, and a line parallel to the bi-pupillary line.

* * * * *